US008579877B2

(12) United States Patent
Gonzalez

(10) Patent No.: US 8,579,877 B2
(45) **Date of Patent: *Nov. 12, 2013**

(54) MEDICAL IV BAG HAVING IMPROVED SHELF LIFE AND VERSATILITY

(75) Inventor: Marcos Gonzalez, Davie, FL (US)

(73) Assignee: Global Harvest Group, Inc., Lynchburg, VA (US)

( * ) Notice: Subject to any disclaimer, the term of this patent is extended or adjusted under 35 U.S.C. 154(b) by 159 days.

This patent is subject to a terminal disclaimer.

(21) Appl. No.: 13/144,192

(22) PCT Filed: Jan. 12, 2010

(86) PCT No.: PCT/US2010/000055

§ 371 (c)(1),
(2), (4) Date: Aug. 17, 2011

(87) PCT Pub. No.: WO2010/080716

PCT Pub. Date: Jul. 15, 2010

(65) Prior Publication Data

US 2012/0029463 A1 Feb. 2, 2012

Related U.S. Application Data

(63) Continuation-in-part of application No. PCT/US2009/000182, filed on Jan. 12, 2009.

(60) Provisional application No. 61/193,950, filed on Jan. 12, 2009.

(51) Int. Cl.
*A61B 19/00* (2006.01)

(52) U.S. Cl.
USPC .......... 604/408

(58) Field of Classification Search
USPC .......... 604/403–416; 206/211; 211/187; 220/254.1, 254.8, 521, 522; 215/228, 215/329, 354
See application file for complete search history.

(56) References Cited

U.S. PATENT DOCUMENTS

| | | | | |
|---|---|---|---|---|
| 4,614,267 | A * | 9/1986 | Larkin | 206/221 |
| 4,936,446 | A | 6/1990 | Lataix | |
| 5,593,028 | A | 1/1997 | Haber et al. | |
| 8,376,157 | B2 * | 2/2013 | Jarvis et al. | 211/187 |

OTHER PUBLICATIONS

International Search Report for International Application No. PCT/US2010/000055, with a mailing date of Apr. 6, 2010.

* cited by examiner

*Primary Examiner* — Philip R Wiest
(74) *Attorney, Agent, or Firm* — Nath, Goldberg & Meyer; Jerald L. Meyer

(57) ABSTRACT

An IV bag including a bladder containing a first substance and a storage cap containing a second substance operable to release the second substance into the bladder to mix with the first substance without exposing the first substance to outside contamination, the storage cap for use with an IV bag including an inner storage chamber for storing a first substance, a first annular opening having a first annular convex surface facing toward the storage chamber, and a plunger element located within the storage chamber having a domed-end with a convex surface facing to the annular opening, wherein the domed end is moveable to make and break contact with the annular opening, and wherein when the domed end is in contact with the first annular convex surface, a seal is formed between two convex surfaces along an annular path to seal the storage chamber.

14 Claims, 8 Drawing Sheets

MEDICAL IV BAG HAVING IMPROVED SHELF LIFE AND VERSATILITY

This is a National Phase Application filed under 35 U.S.C. §371 as a national stage of International Application No. PCT/US2010/000055, filed on Jan. 12, 2010, which claims the benefit under 35 U.S.C. §119(e) of U.S. Provisional Application No. 61/193,950, filed on Jan. 12, 2009, and is a Continuation Application of International Application No. PCT/US2009/000182, filed on Jan. 12, 2009, the content of each of which is hereby incorporated by reference in its entirety.

BACKGROUND

1. Field

This disclosure relates to devices for the storage and mixing of different substances using a portable and inexpensive container, and particularly to intra-venous (IV) bags having special storage devices integrated therein for the storage and mixing of different substances in the IV bag without compromising sterility.

2. Background

There are a plethora of consumer and medical products on the market that have a very limited shelf life, or otherwise depend on refrigeration to extend shelf life to a tolerable extent. For example, the nutritional value of various vitamin-enriched drinks on the market seriously degrades to a small fraction of the original value (when bottled) before such drinks make it to store shelves. Similarly, various medications that must be dissolved in liquid before being administered degrade very rapidly once introduced into the liquid.

While there have been various bottle/container caps, or containers containing multiple chambers to address these issues, such containers suffer from a number of shortcomings. For example, some caps require the puncturing of a membrane separating the different substances to be combined. As a result, there is a likelihood that a portion of the membrane could break off and consequently be ingested. Other solutions that do not involve piercing a membrane have other flaws, such as questionable seals or production difficulty issues.

There are a plethora of different medical products delivered in IV bags. While many of these products, such as saline water, are very stable, there are other products that have a relatively short shelf life and/or require refrigeration. In some situations, this makes providing medical services prohibitively or unduly expensive. For example, for situations where medical triage must be performed for military personnel in remote locations, such as the wilderness of Afghanistan, or emergency medical treatment is needed in remote villages of undeveloped countries, the costs and other resources needed to maintain such perishable items can be prohibitive.

Thus, new technology directed toward containers that accommodate the storage and mixing of different substances is desirable.

SUMMARY

Various aspects and embodiments of the invention are described in further detail below.

In a first series of embodiments, a storage cap for use with a container includes a first structure having a first wall at least partially defining an inner storage chamber operable for storing a first substance, the first wall also defining a first annular opening having a first annular convex surface facing toward the storage chamber, and a second structure coupled to the first structure, the second structure including plunger element located within the storage chamber having a domed-end with a convex surface facing to the annular opening, the domed-end having a radius greater than one-half of the diameter of the first opening, wherein the second structure is configured such that the domed end is moveable to make and break contact with the annular opening, and wherein when the domed end is in contact with the first annular convex surface, a seal is formed between two convex surfaces along an annular path to seal the storage chamber.

In a second series of embodiments, an intravenous (IV) bag for use in medical practices, having a bladder containing a first substance, and a storage cap containing a second substance sealed to the IV bag operable to release the second substance into the bladder to mix with the first substance without exposing the first substance to outside contamination.

BRIEF DESCRIPTION OF THE DRAWINGS

The features and nature of the present disclosure will become more apparent from the detailed description set forth below when taken in conjunction with the accompanying drawings in which reference characters identify corresponding items.

DETAILED DESCRIPTION

The disclosed methods and systems below may be described generally, as well as in terms of specific examples and/or specific embodiments. For instances where references are made to detailed examples and/or embodiments, it should be appreciated that any of the underlying principles described are not to be limited to a single embodiment, but may be expanded for use with any of the other methods and systems described herein as will be understood by one of ordinary skill in the art unless otherwise stated specifically.

For the purpose of this disclosure, the term "storage cap" refers to a device configured to be fastened to a container containing a first substance while itself being capable of separately containing a second substance, and sealing/isolating the first substance from the second substance until such time as an operator, e.g., a doctor, chooses to mix the two substances by mechanically disengaging or removing whatever seal separates the two substances.

Figures 1A, 1B:
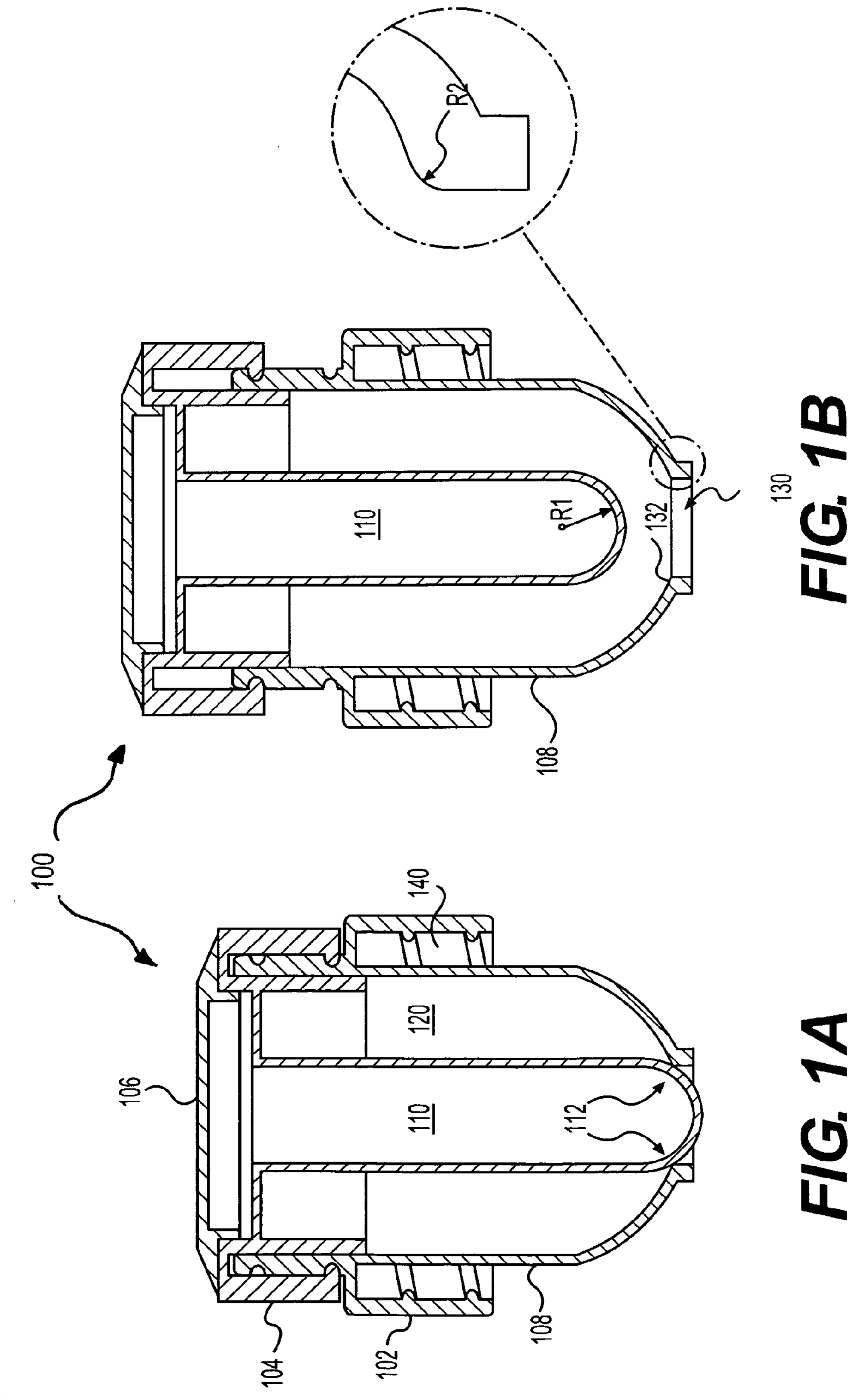
FIGS. 1A and 1B depict details of an exemplary storage cap, shown in cross-sectional view.

FIGS. 1A-1B depict details of a first exemplary storage cap 100. As shown in FIGS. 1A-1B, the exemplary storage cap 100 includes a first wall 102 and an outer wall 108 that at least partially define an inner storage chamber 120, as well as an annular opening 130 at the bottom. The first wall 102 and outer wall 108 also define a threaded chamber 140 for enabling the storage cap 100 to be fastened to a container, such as a plastic bottle with a threaded neck. Generally, the container may be filled with a first substance, such as water, while the first exemplary storage cap 100 is configured to be filled with a second substance, such as a powdered mix, powdered nutritional/vitamin supplement/mixture, or medication. The container and first exemplary storage cap 110 may be bonded together via any number of means, such as ultrasonic welding or via a screw-top fitting, e.g., the same sort of fitting commonly seen between plastic soda bottles with their caps. One advantage of using storage caps is that the shelf life of various consumable drinks and medications can be extended when the active portions of one substance, e.g., vitamins, is in powdered form as compared to situations where such substances would be dissolved in liquid, which may cause the active substances to degrade.

Note that exemplary elements 102 and 108 can be made from a single structure that may be inexpensively produced by the injection molding of various low-cost plastics. Also note that opening 130 is annular and has an inner annular-shaped convex corner 132 having radius R2 with the notion that R2 in the example of FIGS. 1A-1B can be very small as compared to radius R1 of the domed-end of plunger 110, i.e., $R2 \ll R1$, or $R2 \leq R1/10$.

In various other embodiments and as will be shown below, the comparative radii of R1 and R2 may vary greatly in proportion, e.g., $R2/10 \leq R1 \leq 10 \cdot R2$, $R2/5 \leq R1 \leq 5 \cdot R2$, $R2/3 \leq R1 \leq 3 \cdot R2$; $R2/2 \leq R1 \leq 2 \cdot R2$, $R2/1.5 \leq R1 \leq 1.5 \cdot R2$ and $R1 \approx R2$.

Continuing, as shown in FIG. 1B in an 'open' position, a second exemplary storage cap 100 includes a grip 104 connected to the domed plunger 110 with a domed-end again having a radius R1—noting that in practice R1 may be greater than at least half the length of the diameter of opening 130 to assure that the domed-end can form a seal with opening 130 at edge 132 (contact points 112 of FIG. 1A). Note that exemplary elements 104 and 110 also can be made from a single structure (e.g., a single piece of uniform plastic) that may be inexpensively produced by the injection molding of various low-cost plastic materials. Also note that the two singular structures are configured such that the domed-end of plunger 110 is moveable to make and break contact with the annular opening 130, and a seal may be made or broken by twisting grip 104 relative to walls 102 and 108.

Figure 2:
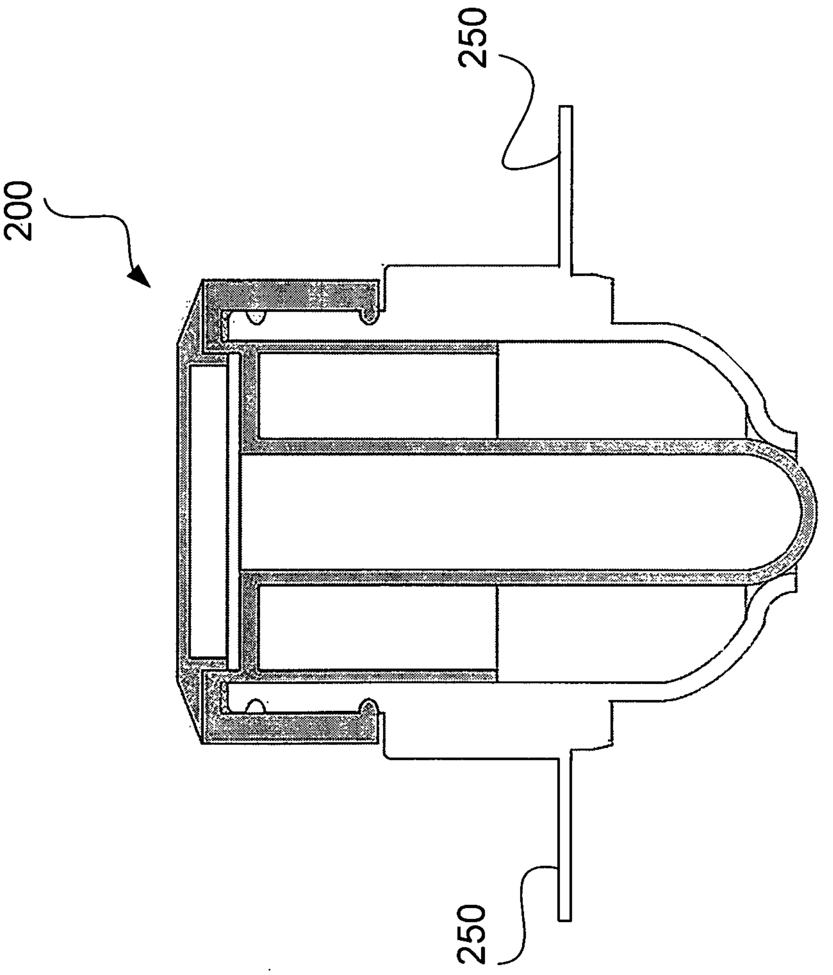
FIG. 2 depicts an exemplary modified storage cap, shown in cross-sectional view.

FIG. 2 depicts a modified version of the storage cap 100 of FIG. 1. As shown in FIG. 2, the exemplary modified cap 200 is essentially the same as the example of FIG. 1, but the threaded chamber 140 is replaced with a flange 250 useful to allow storage cap 200 to be welded (ultrasonically, by heat or otherwise) or otherwise incorporated onto a sheet of plastic, such as any of the plastics used to make IV bags.

Figure 3B:
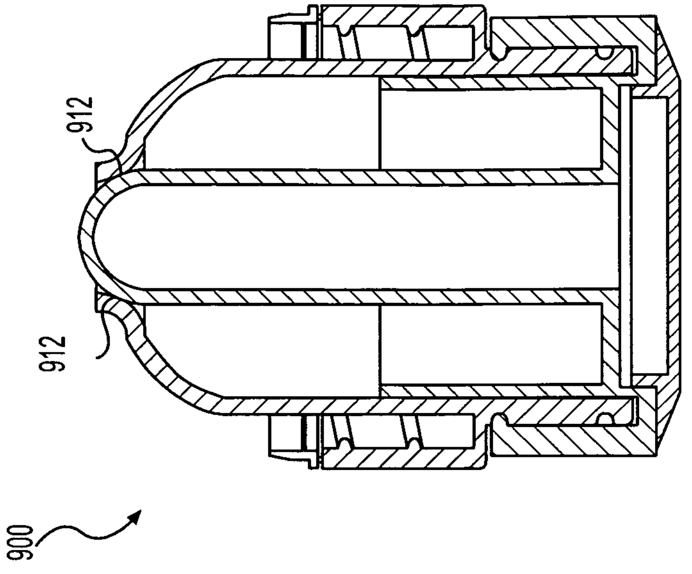
FIGS. 3A and 3B depict details of another exemplary storage cap.
Figure 3A:
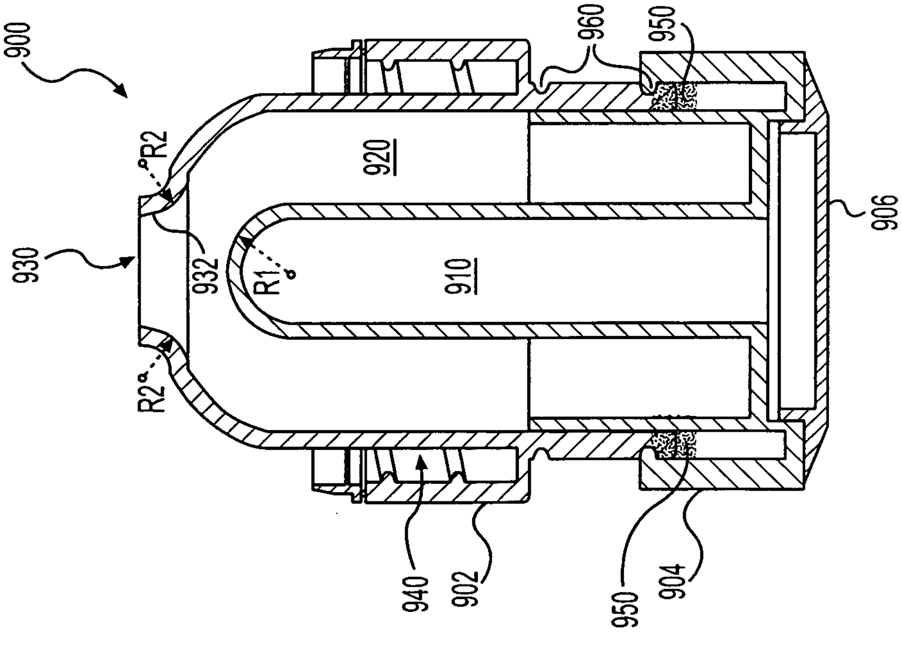

FIGS. 3A and 3B depict details of another exemplary storage cap 900. As shown in FIG. 3, storage cap 900 includes elements 902-932 that are generally identical to respective elements 102-132 of FIGS. 1A-1B, such as cap top 906 relative to 106 of FIG. 1A, but with some notable differences. For example, edge 132 of FIGS. 1A-1B is replaced with a more rounded convex surface 932 (convex relative to the storage chamber 920 and plunger 910), which may have an advantages in manufacturing tolerances, use of plastic materials and reliability. Also, an optional gasket 950 between the two singular structures may be added to improve isolation of any stored substances in chamber 920 with the exterior environment. Recessed lip 960 further enhances substance isolation.

Figure 4A:
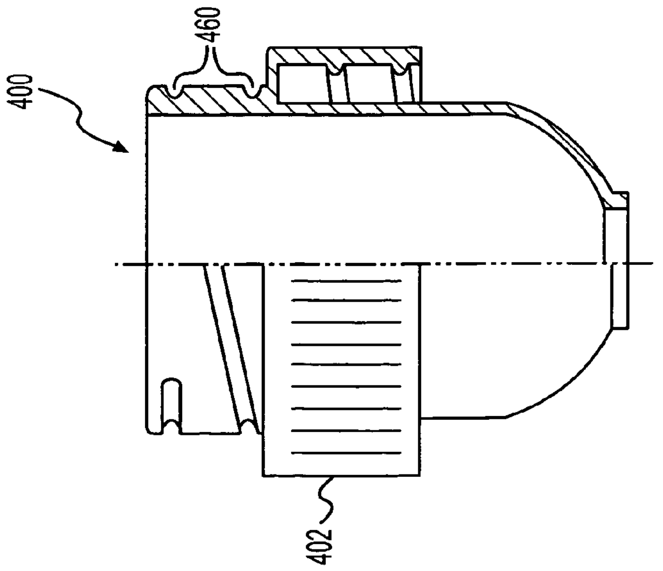
FIGS. 4A-4C depict further details of an exemplary storage cap.
Figure 4B:
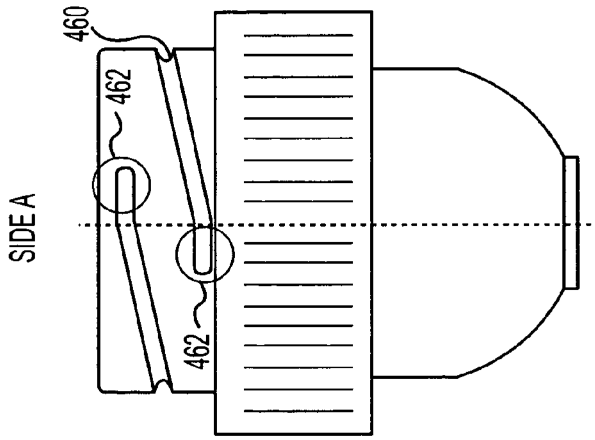
Figure 4C:
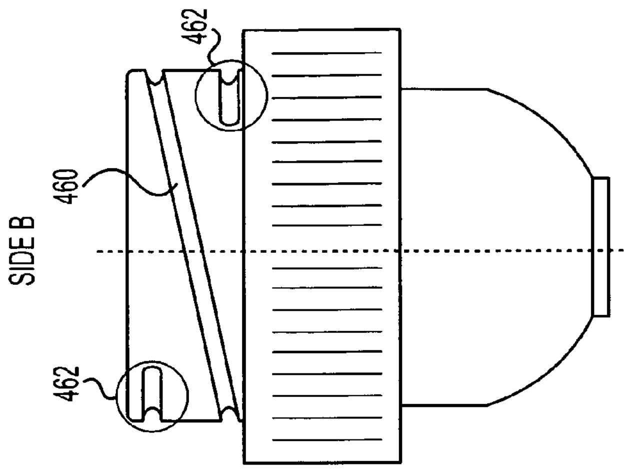
Figure 5A:
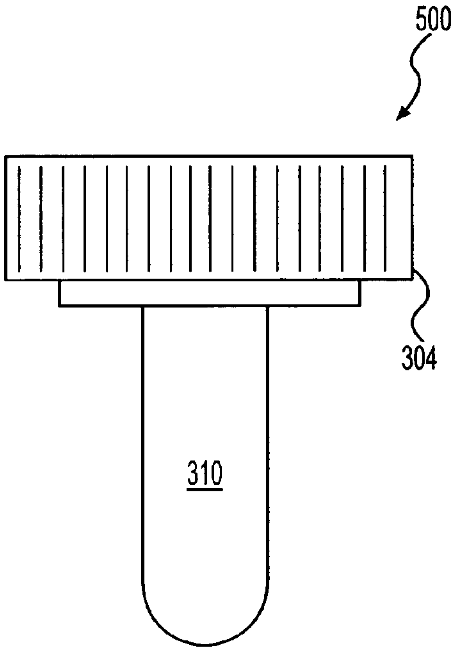
FIGS. 5A-5D depict still further details of an exemplary storage cap.
Figure 5B:
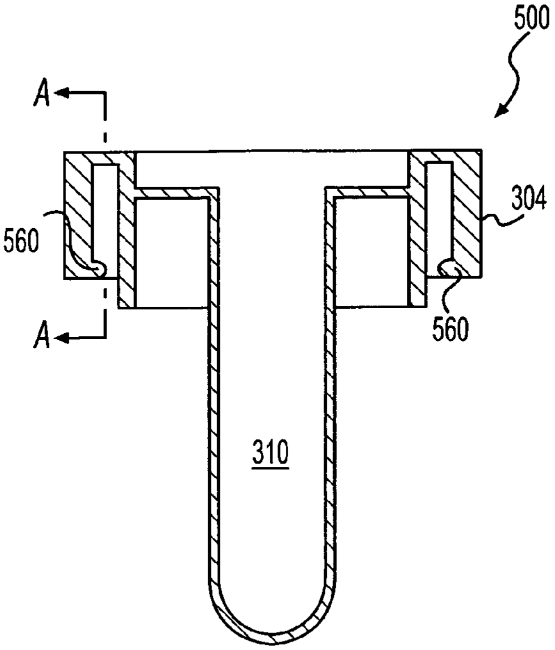
Figure 5C:
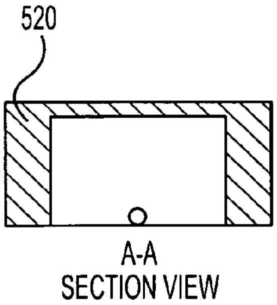
Figure 5D:
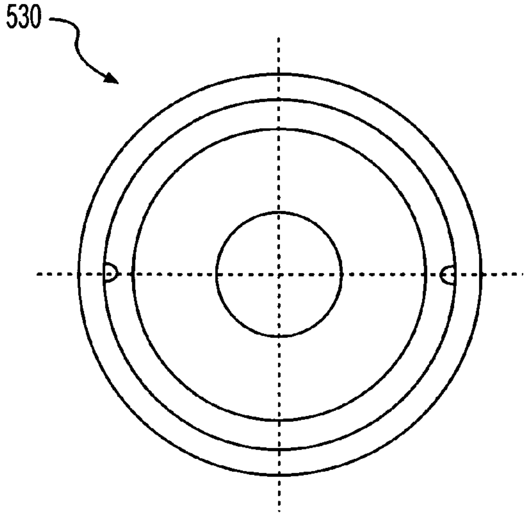

FIGS. 4A-4C depict further details of an exemplary storage cap, defined for convenience here as a first "singular structure" 400, with emphasis on screw threads 460 noting that the end portions 462 of threads 460 may act to help lock structure 400 relative to structure 500 (of FIGS. 5A-5D) and/or to preclude the range of motion of plunger 410 relative to opening 430. Other locking and/or limiting mechanisms, such as detent structures built into structures 400 and or 500, may also be used separately or together with the exemplary thread shape of FIGS. 5A-5C.

FIGS. 5A-5D depict still further details of the second exemplary storage cap defined for convenience here as a the second "singular structure" 500, with emphasis on screw threads 560 usable with threads 460 of FIGS. 4A-4C. Cross-sectional view 520 and top view 530 are also added for better clarity.

Another advantage besides simplicity of manufacturing and reliability of the examples of FIGS. 1A-5D is the relative ease of filling and sealing the devices as compared to other storage caps. For example, when device dimensions are made to comply with standard opening sizes for various containers, suppliers can use the example caps of FIGS. 1A-5D with little or no retooling and/or use off-the-shelf assembly line techniques and devices. Accordingly, costs can be substantially reduced.

Figure 6:
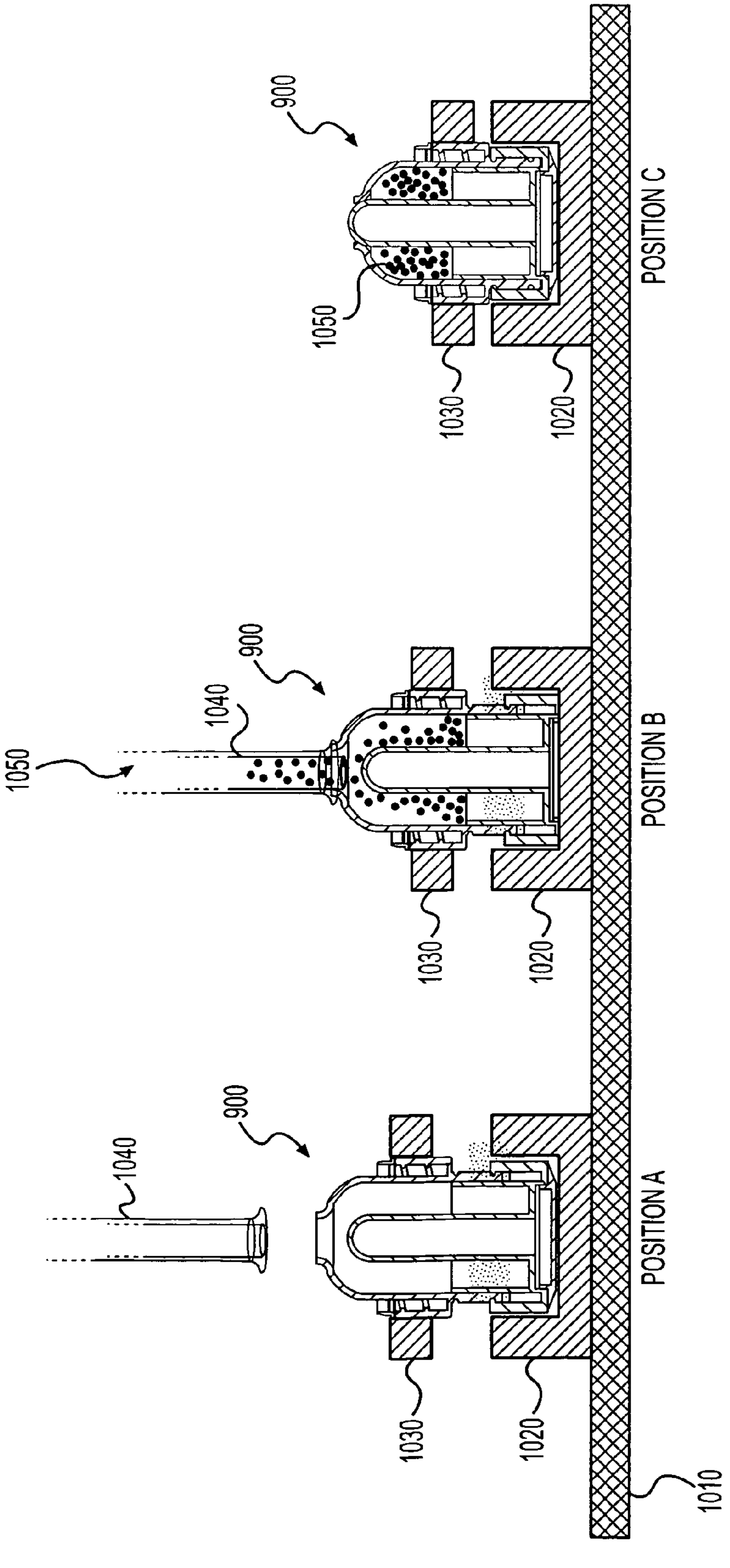
FIG. 6 depicts an exemplary filling process for the storage caps of FIGS. 1A-5D, using an exemplary supply nozzle, shown in cross-sectional view.

FIG. 6 depicts a filling process for any of the caps of FIGS. 1A-5D. An exemplary process is shown in FIG. 6, respective to a conveyer belt 1010 having three positions A, B and C (provided for reference only), the conveyer belt configured to convey a device holder comprising a first gripping element 1020, a second gripping element 1030 and a supply tube 1040.

In operation, an exemplary storage cap 900 can be placed within gripping elements 1020 and 1030 at Position A of conveyer belt 1010, such that the opening aligns with supply tube 1040. Note that storage cap 900 is not sealed at this position.

Next, at Position B, supply tube 1040 is lowered to make contact with the annular opening of storage cap 900 such that a flange or other sealing element (explained further below) can effectively seal the storage chamber of cap 900 relative to the exterior of storage cap 900. Then, a substance 1050 can be injected into the storage chamber of storage cap 900 while displaced air from the storage chamber is vented. Upon filling the storage chamber, storage cap 900 is brought to position C where gripping elements 1020 and 1030 can be made to rotate/twist relative to one another and thus cause the storage cap 900 to be sealed against external conditions/environment as the two singular structures discussed above rotate/twist relative to one another causing the convex surfaces of the internal plunger and annular opening to meet, to form a seal.

After filling a particular storage cap, that storage cap may be sealed or otherwise incorporated into a container, including for example an IV bag.

It should be appreciated that, for the example of FIG. 6, the term "position" is depicted in terms of relative position. However, for other examples, the term may be thought of in spatial terms or alternately may be thought of in terms of manufacturing steps. For example, the steps depicted in Positions A, B and C may all occur at a single location depending on the particular manufacturing equipment used. Also, the term "position" may encompass more that a point in space but may alternately encompass a space or distance. For example, the filling process of Position B may take place as storage cap 900 moves continuously along conveyer belt 1010 over a distance of one meter.

Figure 7:
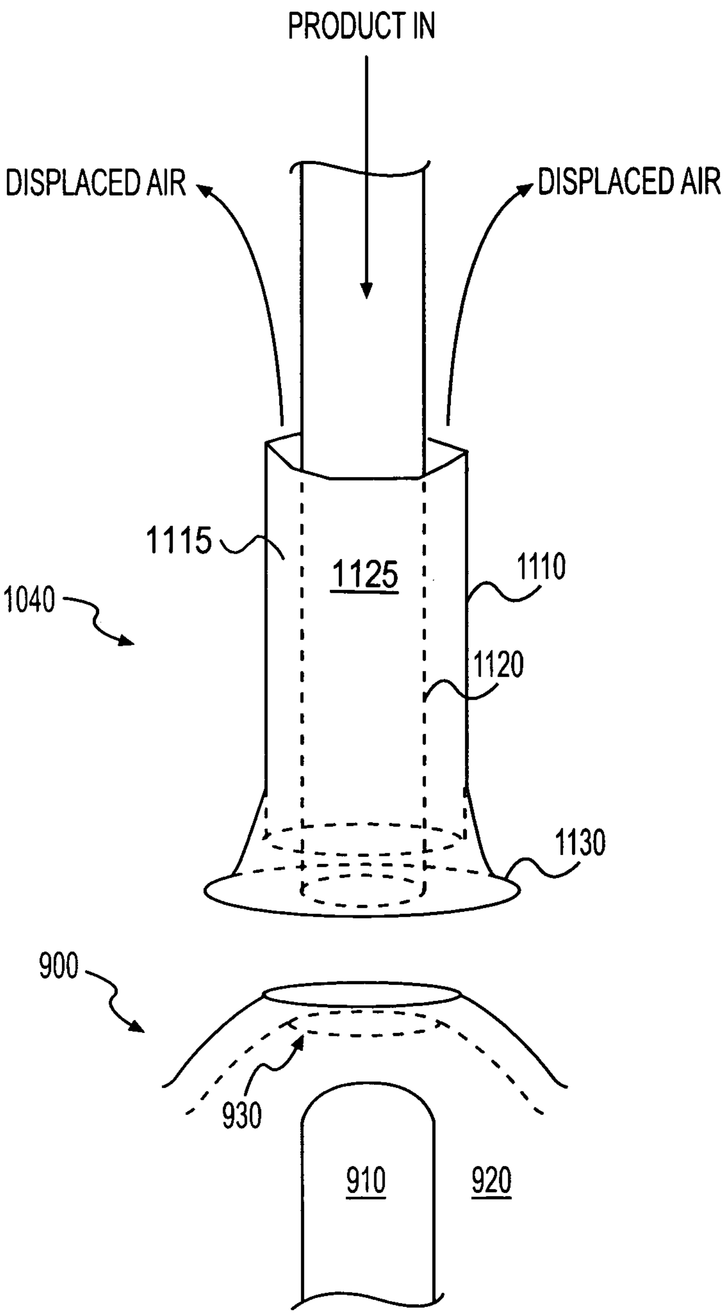
FIG. 7 depicts further details of the exemplary supply nozzle of FIG. 6.

FIG. 7 depicts further details of an exemplary supply tube 1040 that may be used in the process shown in FIG. 6. As shown in FIG. 7, the exemplary supply tube 1040 includes an outer wall 1110 and an inner wall 1120 defining a supply passage 1125 and a displaced-air passage 1115. A flange 1130 is also included to seal the opening 930 of storage cap 900 from the exterior environment while a product is supplied to storage chamber 920 via supply passage 1125 and displaced air is vented via the displaced-air passage 1115.

Note that in alternate embodiments, the supply passage 1125 and displaced-air passage 1115 can take a variety of different physical configurations. For example, the particular functions of passages 1125 and 1115 may be exchanged, so that passages 1125 and 1115 may be formed using tubes adjacent to one another and/or multiple tubes may be used to replace single tubes for either or both passages 1125 and 1115.

Looking at the plunger 910 in FIG. 7, it is to be appreciated that its domed-shaped end has another advantage (besides creating an effective seal) in that the domed-end facilitates the process of filling storage space 920 in that any powder or liquid dropped through passage 1125 can smoothly flow down and around the dome with little likelihood of any substantial amount of deposited product might stick to or otherwise be trapped at a critical location, such as that point of plunger 910 that would make contact with annular opening 930 to form a seal.

Figure 8:
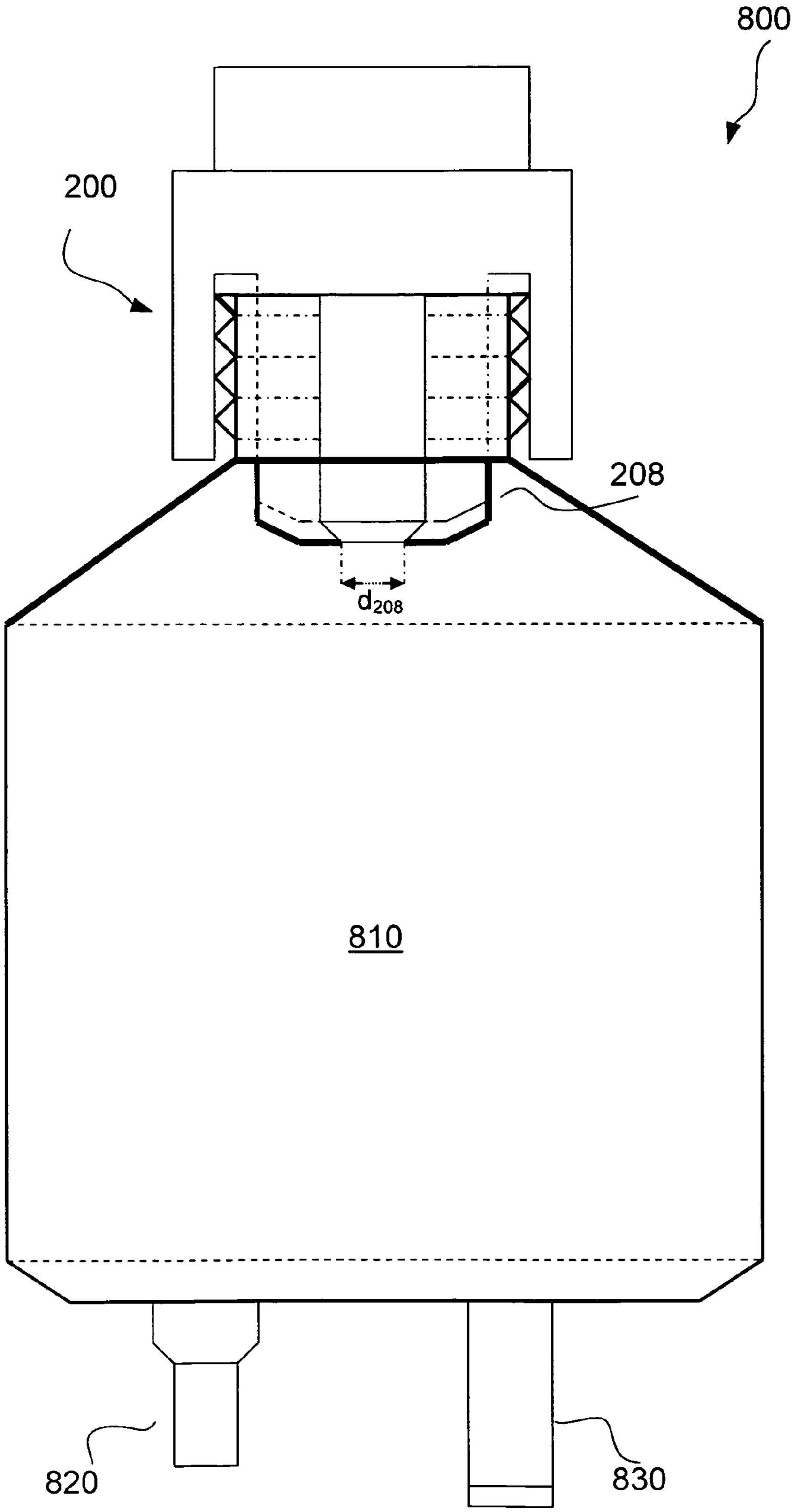
FIG. 8 depicts an exemplary IV bag incorporating an exemplary storage cap.

FIG. 8 depicts an exemplary IV bag 800 incorporating the storage cap 200 of FIG. 2—assuming to be incorporated for this example by ultrasonic welding as discussed above, so that in one embodiment, a sterile barrier receiver cup 208 is essentially molded within the bag. In an alternative embodiment, storage cap and IV bag can be injection molded together, forming a single-molded design. The IV bag bottom may be molded and then extended, allowing for release of air. IV bag materials are well-known in the art. As shown in FIG. 8, the IV bag includes a storage bladder 810, outlet tubes 820 and 830 and storage cap 200. An optional handle is not shown. In one embodiment, the receiver cup inlet port diameter $d_{208}$ may match the diameter of the cap plunger to effect optimum sealing.

In operation, an operator may mix the contents of bladder 810 and storage cap 200 by twisting/rotating the two major structural components of cap 200 relative to one another, thus removing its plunger from its respective annular opening to break the seal created there between. After the substances have had time to properly mix, the IV bag 800 may be used to administer the resultant mixture to a patient noting that the above-described process enables the IV bag 800 to have a relatively long shelf life and that mixing occurs without threat of contamination of the mixture by outside elements.

Note that, in various embodiments, storage cap 200 may benefit from having any number of seals, such as a tamper-proof cover, a breakable seal tab or heat-shrink plastic, to help keep the two main portions from rotating relative to one another (due to handling or ambient vibration) before use to assure quality and deter tampering.

An advantage to using the particular storage cap (or derivatives thereof) with medical devices, such as IV bags, is that the cap can form surprisingly high-quality seals while being very inexpensive to manufacture. Thus, appropriate mixing may occur without exposing the (presumed) sterile substances to the outside world.

What has been described above includes examples of one or more embodiments. It is, of course, not possible to describe every conceivable combination of components or methodologies for purposes of describing the aforementioned embodiments, but one of ordinary skill in the art may recognize that many further combinations and permutations of various embodiments are possible. Accordingly, the described embodiments are intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

It will be understood that many additional changes in the details, materials, steps and arrangement of parts, which have been herein described and illustrated to explain the nature of the invention, may be made by those skilled in the art within the principal and scope of the invention as expressed in the appended claims.

What is claimed is:

1. An intravenous (IV) bag for use in medical practices, comprising:

a bladder containing a first substance; and a storage cap containing a second substance sealed to the IV bag, said storage cap positoned to release the second substance into the bladder to mix with the first substance without exposing the first substance to outside contamination, the storage cap comprising:

a first structure having a first wall at least partially defining an inner storage chamber operable for storing the second substance, the first wall also defining a first annular opening having a first annular convex surface facing toward the storage chamber; and a second structure coupled to the first structure, the second structure including a plunger element located within the storage chamber and having a domed-end with a convex surface facing toward the annular opening, the domed-end having a radius greater than one-half of the diameter of the first opening;

wherein the second structure is configured such that the domed end is moveable to make and break contact with the annular opening, and wherein when the domed end is in contact with the first annular convex surface, a seal is formed between the two convex surfaces along an annular path to seal the storage chamber.

2. The IV bag of claim 1, wherein the first structure also includes a structure operable to enable the storage cap to be fastened at an opening of the IV bag such that the first opening is sealed within the IV bag, wherein the structure is a first threaded twist-top structure operable to enable the storage cap to be fastened to the IV bag via a twisting action relative to the IV bag.

3. The IV bag of claim 1, wherein the first structure is made from a single piece of plastic, and wherein the second structure is also made from a single piece of plastic.

4. The IV bag of claim 1, wherein the radius of the domed-end R1 is greater than the radius of the first annular convex surface R2.

5. The IV bag of claim 4, wherein the first annular convex surface is essentially a corner compared to the radius of the domed-end.

6. The IV bag of claim 5, wherein the radius of the domed-end R1 has a proportion to the radius of the first annular convex surface R2 of a range: $R2/10 \leq R1 \leq 10 \cdot R2$.

7. The IV bag of claim 6, wherein the radius of the domed-end R1 has a proportion to the radius of the first annular convex surface R2 of a range: $R2/3 \leq R1 \leq 3 \cdot R2$.

8. The IV bag of claim 7, wherein the radius of the domed-end R1 has a proportion to the radius of the first annular convex surface R2 of a range: $R2/1.5 \leq R1 \leq 1.5 \cdot R2$.

9. The IV bag of claim 1, wherein the second structure is coupled to the first structure via a threaded structure.

10. The IV bag of claim 9, wherein the second structure is coupled to the first structure via a second threaded twist-top structure such that twisting a grip on the second structure relative to the first structure causes the domed-end to move closer or farther away from the annular opening.

11. The IV bag of claim 10, wherein the second threaded twist-top structure includes at least one locking structure to hold the second structure at a first secure angle relative to the second structure.

12. The IV bag of claim 10, further comprising a gasket between the first structure and the second structure operable to improve the seal of the storage chamber.

13. The IV bag of claim 1, wherein:

the first structure also includes a first threaded twist-top structure operable to enable the storage cap to be fastened to the IV bag via a twisting action relative to the IV bag; and the second structure is coupled to the first structure via a second threaded twist-top structure such that twisting a grip on the second structure relative to the first structure causes the domed-end to move closer or farther away from the annular opening.

14. The IV bag of claim 13, wherein:

the second threaded twist-top structure includes at least one locking structure to hold the second structure at a first secure angle relative to the second structure; and a gasket exists between the first structure and the second structure operable to improve the seal of the storage chamber.

* * * * *